(12) United States Patent
Lazzari et al.

(10) Patent No.: US 9,206,389 B2
(45) Date of Patent: Dec. 8, 2015

(54) CULTURE FOR EXPANDING STEM CELLS EX-VIVO

(75) Inventors: Lorenza Lazzari, Milan (IT); Tiziana Montemurro, Milan (IT); Rosaria Giordano, Milan (IT); Paolo Rebulla, Milan (IT); Girolamo Sirchia, Milan (IT)

(73) Assignee: Fondazione IRCCS Ca' Granda-Ospedale Maggiore Policlinico, Milan (IT)

( * ) Notice: Subject to any disclaimer, the term of this patent is extended or adjusted under 35 U.S.C. 154(b) by 1021 days.

(21) Appl. No.: 12/668,818

(22) PCT Filed: Jul. 9, 2008

(86) PCT No.: PCT/IB2008/001798
§ 371 (c)(1),
(2), (4) Date: Feb. 12, 2010

(87) PCT Pub. No.: WO2009/010841
PCT Pub. Date: Jan. 22, 2009

(65) Prior Publication Data
US 2010/0189700 A1    Jul. 29, 2010

(30) Foreign Application Priority Data

Jul. 16, 2007   (IT) .............. MI2007A1421

(51) Int. Cl.
   *C12N 5/00*      (2006.01)
   *C12N 5/073*     (2010.01)
   *C12N 5/078*     (2010.01)
   *A61K 35/12*     (2015.01)

(52) U.S. Cl.
   CPC ............ *C12N 5/0018* (2013.01); *C12N 5/0603* (2013.01); *C12N 5/0634* (2013.01); *A61K 2035/124* (2013.01); *C12N 2501/125* (2013.01); *C12N 2501/145* (2013.01); *C12N 2501/23* (2013.01); *C12N 2501/26* (2013.01)

(58) Field of Classification Search
None
See application file for complete search history.

(56) References Cited

U.S. PATENT DOCUMENTS 5,397,706 A *   3/1995   Correa et al. ................ 435/406
7,109,032 B2 *  9/2006   Cancedda et al. ............ 435/404

FOREIGN PATENT DOCUMENTS

WO   2005/007799   1/2005

OTHER PUBLICATIONS

Araceli Encabo, et al., Selective Generation of Different Dendritic Cell . . . , Stem Cells, vol. 22, No. 5, pp. 725-740, XP002510073.
Lesley J. Murray, et al., Thrombopoietin, FLT3, and Kit Ligands Together Suppress . . . , Experimental Hematology, vol. 27, No. 6, pp. 1019-1028, 1999.
Santoni De Sio, et al., 1038., Lentiviral Gene Transfer Into HSC Is Enhanced by Early-Acting . . . , Molecular Therapy, vol. 11, pp. 401.
Toni Peled, et al., Linear Polyamine Copper Chelator Tetraethylenepentamine . . . , Experimental Hematology, vol. 32, No. 6, pp. 547-555, 2004, XP002510075.
S. Bruno, et al., Different Growth Factor Requirements for the Ex Vivo . . . , Journal of Biological Regulators and Homeostatic Agents, vol. 15, No. 1, pp. 38-48, 2001, XP009110635.

* cited by examiner

*Primary Examiner* — Blaine Lankford
(74) *Attorney, Agent, or Firm* — Silvia Salvadori, P.C.; Silvia Salvadori

(57) ABSTRACT

The present invention relates to a culture including a growth medium and a combination of cytokines consisting of i) interleukin-6 (IL6); ii) flt3-ligand (FLT3); iii) stem cell factor (SCF) and iv) thrombopoi-etin (TPO); the use of the culture for expanding. ex vivo stem cells and/or parental cells and cells differentiated therefrom, and the use of said cells obtainable from said expansion.

13 Claims, No Drawings

CULTURE FOR EXPANDING STEM CELLS EX-VIVO

CROSS-REFERENCE TO RELATED APPLICATIONS

This application is a 371 of PCT/IB2008/001798 filed on Jul. 9, 2008, which claims the benefit of Italian Patent Application No. MI2007A001421 filed on Jul. 16, 2007, the contents of each of which are incorporated herein by reference.

The present invention relates to a culture including an expansion medium and a cytokine composition consisting of i) interleukin-6 (IL6); ii) flt3-ligand (FLT3); iii) stem cell factor (SCF) and iv) thrombopoietin (TPO), its use for expanding ex vivo stem cells and/or parental cells and cells differentiated therefrom and the use of said cells obtainable from said expansion.

It is known that stem cells and/or parental cells potentially have revolutionary applications in the field of the regenerative medicine and in other fields of medicine and biology. Amongst the application examples known in the art, the most studied and defined at a clinical level is the bone marrow transplantation, even if there are other kinds of therapies as the transplantation of mesenchymal stem cells in the degenerated joints.

A problem arising from the application of stem cells and/or parental cells is represented by the reduced number of available cells at the time of the application. There are protocols known in the art for increasing the number of said stem and/or parental cells. The increase of stem and/or parental cells occurs through the division of a mother stem cell in at least two daughter cells. An example of a protocol known in the art for increasing the number of stem cells is the use of a feeder layer. However, said protocols present a second problem, as they are not able to maintain the maturation state in the daughter stem cells similar to the maturation state of the mother stem cell. Maturation state means, in the context of the present invention, the total genotype and/or phenotype state of a cell.

A parameter used in the context of the present application for measuring the maturation of cells resulting from one or more division steps is the probability of self-maintenance (or Psm). The Psm value can be represented from the following formula:

$$Psm = \frac{\text{Number of daughter cells similar in genotype and phenotype properties to a mother stem cell resulting from an expansion and/or differentiation of the same mother stem cell}}{\text{Number of total cells resulting from an expansion and/or differentiation of a mother stem cell}}$$

Psm can vary between 0 and 1 and its value depends on multiple factors, among which the number of daughter cells, the kind of division and the number of division steps.

For example, if only one of the daughter cells retains the maturation state of the mother stem cell in a single division step, the Psm for the single step is 0.5. In the context of the present invention, the Psm value, can be applied to a single cell or as an average of the division of a plurality of cells, keeping into account only stem and/or parental cells, and not, for example, cells more differentiated and without regenerative power which can result therefrom.

It is known in the art that the expansion of stem and/or parental cells involves, besides their expansion, a differentiation of the stem cells in differentiated cells. In the context of the present invention, differentiation means that a daughter cell has different genotype and phenotype properties with respect to the mother cell and therefore it lowers the resulting Psm value.

In the context of the present invention, all methods known in the art for quantifying the maturation of the cells are applicable. The method to be applied mainly depends on the type of stem cell to be expanded. A preferred method is that of flow cytometry, such as for example Beckton-Dickinson FACS. An example of said method is the one of measuring the maturation state of haematopoietic stem cells, in which the presence of the marker proteins $CD34^+CD133^+CD45^{+/-}$ on the cells is measured.

Some protocols have been proposed in the art, in which there is described the expansion of stem cells in a growth or division step of the mother cells, with a Psm equal to 0.5. This means that for each division step of the stem cells, a daughter cell retains the same maturation state of the mother stem cell, but the other one is differentiated. Said protocols, however, do not meet the demanded requirements since the protocols allow to expand the stem cells with a Psm of 0.5 only for one or two generations. After the first or second division step, the Psm value is drastically lowered. By "generations", in the context of the present invention, it is meant the number of division steps of at least one mother stem cell. Therefore, said protocols do not give satisfactory results, as the Psm only lowers after two generations and consequently the total increase of stem and/or mother cells is relatively low and the total growth is not exponential.

An example in which the problems above mentioned concerning the application of stem and/or mother cells are well pointed out is in the transplantation of haematopoietic stem cells and/or mother cells from umbilical cord blood. The umbilical cord blood is allogenic or autologous and rich in haematopoietic stem cells. Haematopoietic stem cells are used in the "bone marrow transplantation" of humans with an ablated or reduced haematopoietic system because of pathologies or therapies consequent to some pathologies. The reduced number of haematopoietic stem cells and/or mother cells which can be used determines a consequent problem of reduced effectiveness: this is known in the art and proved by the fact that the bone marrow trans-plantations from umbilical cord blood are mainly performed on patients of a reduced weight. A second problem is the maturation state of the cells: haematopoietic stem/parental cells are at an immature state in the umbilical cord blood and this allows the post-transplantation rooting within the bone marrow. Without said rooting in the bone marrow, there is an undesired immune vulnerability in the patients. The problem is that the number of stem cells with the desired maturity for the rooting is too low for the patient requirement. Therefore, it is necessary to maintain the similar maturation state in the expanded haematopoietic stem/parental cells, so as to allow to said expanded cells to rapidly take root in the bone marrow and start to play their protective role in a short time.

The Applicant has surprisingly found that the solution to the problems above mentioned includes the use of a combination of cytokines existing in a culture including an expansion medium.

Aim of the present invention is a combination of cytokines existing in a culture including an expansion medium. Said combination of cytokines consists of:
 i) interleukin-6 (IL6)
 ii) flt3-ligand (FLT3)

iii) stem cell factor (SCF)

iv) thrombopoietin (TPO)

Said culture, including the combination of cytokines and the growth medium for growing or maintaining viable stem and/or parental cells, includes in its definition industrial scale bioreactors.

In the context of the present invention, by "stem cells" it is meant cells having the following features:

they are highly immature or non differentiated, they are capable of proliferation and at the same time self-maintenance or self-renewal, and they are capable of generating daughter cells of the same or a different kind.

Stem cells are mammalian totipotent, pluripotent or multipotent cells known in the art. Totipotent stem cells are cells capable of renewing and capable of differentiating in cells of the three germ layers, endodermis, mesodermis and ectodermis, for finally forming a whole new organism. Pluripotent stem cells are differentiated from totipotent cells and all retain their abilities, except of being able to form, only starting from pluripotent cells, a complete organism. Multipotent stem cells are stem cells which are able to produce cells of a common or similar phylogeny, such as for example haematopoietic stem cells which form all the cells of the haematopoietic system or as mesenchymal stem cells which form stromal cells, belonging to bone and/or fat tissues.

Optionally, stem cells according to the invention do not include totipotent stem cells resulting from a *Homo sapiens* embryo.

Optionally, stem cells according to the invention do not include stem cells resulting from a *Homo sapiens* embryo.

Within the definition of stem cells there are also in cluded parental cells, namely cells capable of developing in a single kind of cell or in cells of a closely related, such as for example lymphoid cells and plasma cells or endothelial cells, which retain the ability of renewing themselves. An example of a parental cell is the satellite cell, which is able to melt and increase the total mass of cells belonging to a muscle.

The growth medium existing in the culture according to the invention can be any medium known in the art capable of providing the essential nutrients to cells, in such a way that they can expand. Preferably, the growth medium does not include other factors besides those above listed and then reported in Table 1, known in the art for having a stimulating effect on the growth of stem cells.

An advantage of the combination of cytokines existing in a culture including an expansion medium according to the invention resides in its simplicity and in that other factors, possibly responsible of the change of the maturation state, are not present. Said advantage is well pointed out when compared to growth media known in the art, such as for example a feeder layer, in which there is a contamination with other "foreign" cells, wherein there is not reproducibility and consequently the expansion is not a standardized process and stem cells are stimulated to differentiate themselves in myeloid cells.

In a preferred embodiment, the growth medium is liquid. An example of a medium known in the art is Cell Gro SCGM (CellGenix, Freiburg, Germany) or its derivatives. In preferred embodiments, cytokines are present in said growth medium at the concentrations as reported in Table 1:

TABLE 1

Concentrations of cytokines according to the invention existing in the liquid growth medium

| Cytokine according to the invention | Cytokine concentration in a liquid growth medium (ng/ml) |
|---|---|
| Interleukin-6 (IL6) | 1-20, preferably 5-15, still more preferably 9-11 |
| flt3-ligand (FLT3) | 20-80, preferably 35-65, still more preferably 49-51 |
| Stem cell factor (SCF) | 20-80, preferably 35-65, still more preferably 49-51 |
| thrombopoietin (TPO) | 1-20, preferably 5-15, still more preferably 9-11 |

In a preferred embodiment, the growth medium according to the invention does not include any serum. The use of a medium free of serum is advantageous since it allows to reduce the possibility of contaminations (contaminations with factors affecting the maturation state of the stem cells during the expansion) and/or reduce the possibility of Infections within the medium.

Another aspect of the invention is a method for expanding stem cells in which there is at least a step in which stem cells are contacted with the culture, preferably mixed within the culture, according to the invention as above described. Said method is carried out ex vivo and with equipments known in the art for preparing cell populations in cultures.

Said step for expanding the cells according to the invention preferably has a Psm value equal or higher than 0.4, and preferably equal or higher than 0.5 for at least 3 generations of stem cells, preferably at least 5 generations, more preferably 8 generations, more preferably 10 generations, more preferably 12 generations, more preferably 15 generations, more preferably 18 generations, still more preferably 20 generations. The Psm can preferably be equal or higher than 0.4, preferably equal or higher than 0.5 for 50 generations.

Alternatively, said cell expansion can be defined with the fold expansion parameter. The method can preferably expand stem cells at least 5 times, preferably at least 10 times, more preferably at least 15 times and still more preferably 20 times the number of initial cells in 2 weeks. Cells can expand themselves up to 60 times the number of initial cells in 2 weeks. When there are included also differentiated cells, with or without the resulting regenerative potentials, said method can preferably expand the cells from 180 to 650 times the number of initial cells in 2 weeks, preferably from 200 to 650 times the number of initial cells. The analysis of the produced cell population is performed with methods known in the art, such as counting with the Burker chamber or preferably flow cytometry as above mentioned. For the fold-expansion, the multiplication of the resulting population relative to the initial one is measured.

In a preferred version, cells are expanded with an haematoangio chain, that is haematopoietic and endothelial from a "mother" cell in common. Preferably, cells expanded according to said embodiment are $CD34^+133^+45^+$ (haematopoietic cells) and $CD34^+133^+45^-$ (endothelial cells). Said cells can be selected with any methods known in the art for selecting cells, such as for example with the CliniMACS system, Miltenyi Biotech, Bergisch Gladbach, Germany.

In an embodiment of the method according to the invention, the cell expansion using the culture according to the invention is not limited to a number of generations and can continue in an indefinite way. Said embodiment of the method includes obvious alterations for rendering the same more lasting, which are however known to the skilled in the art, such as for example including steps of cell passages when one arrives to the confluence and restore of the medium and the cytokines. Said method can expand stem cells independently from the number of generations, preferably with a Psm equal or higher than 0.4, more preferably equal or higher than 0.5.

In a still more preferred embodiment of the method according to the invention, in said passage stem cells are put in a culture according to the invention at a concentration initially between 1000 cells/ml and 10000 cells/ml, preferably between 3500 cells/ml and 6500 cells/ml in a liquid growth medium, more preferably in a serum-free medium, such as Cell Gro SCGM (CellGenix, Freiburg, Germany) or its derivatives. Said expansion has not maximum time limits and the length depends on the way the skilled in the art has applied the method. Preferably, the method lasts from 10 days to 60 days, more preferably from 12 to 30 days and still more preferably from 13 to 24 days. During said method, the concentrations of cytokines existing in the culture according to the invention are preferably returned in their starting concentration, as reported in Table 1, at least twice a week.

Said method can preferably expand stem cells, preferably with a Psm equal or higher than 0.4, more preferably equal or higher than 0.5 for at least 20 generations in 2 weeks, preferably from 26 to 60 generations the number of initial cells in 2 weeks. Alternatively, cells are expanded with a fold expansion of 20 fold from 26 to 60 times in two weeks. When also the resulting differentiated cells, are included, said method can preferably expand the cells in at least 50 times the number of initial cells in 2 weeks, preferably from 180 to 650 times the initial cell number.

In preferred embodiments of said method, one works under sterile conditions, such as for example with a sterile hood, and the population of cells obtainable from said embodiment contains an endotoxins level under the limit of 0.05 IU/ML (European Pharmacopoeia) and does not show mycoplasma or bacterial mycotic contaminations.

Another advantage of the use of the culture according to the invention or the methods as above mentioned is that the resulting cells do not present altered karyotypes and do not give rise to tumors when successively implanted.

In an embodiment of the method, the resulting cells are frozen after the expansion step. Said step can use freezing methods of stem cells known in the art, such as for example the introduction of the expanded cells in a solution containing 10% v/v of dimethyl sulfoxide, 70% v/v of autologous plasma (preferably irradiated with 2500 rad) and 20% v/v of a commercially available medium and then freezing of the resulting solution.

In other preferred embodiment of the method according to the invention, the method of expansion of the stem cells can be incorporated in a method for preparing a medicament as below described. The preparation of the medicament can be carried out after, preferably immediately after the expansion step of the cells. Alternatively, said medicament can be produced after the thawing of an aliquot of cells frozen as above described. In the preparation of the medicament it is preferable to use cells which have been preventively separated from the cytokines. All methods known in the art for separating cytokines are contemplated, such as for example the centrifugation in which the cytokines remain in the supernatant and the cells within the pellet.

According to another aspect, the present invention relates to cells obtainable from the method according to the invention and their uses. Obtainable cells include stem cells in a higher number and with a genotype and/or phenotype profile equal to that of the parent cells. Said resulting cells are obtainable from a process characterized by a number of Psm equal to or higher than 0.4, preferably equal to or higher than 0.5, independently of the number of expanded generations, besides being characterized by the absence of alterations of the karyotype and the absence of tumors in the resulting cells. In a preferred embodiment, said cells are present in a composition together with the cells differentiated therefrom and in a sufficient quantity for allowing their application in therapeutic processes as below mentioned.

In an embodiment of said aspect of the invention, cells are present in a frozen aliquot. Said aliquot includes said cells obtainable according to the method of the invention as above described and compositions known in the art for maintaining viable the cells when frozen, preferably those containing from 5 to 20% v/v of dimethyl sulfoxide, for example a solution containing 10% v/v of dimethyl sulfoxide, 70% v/v of autologous plasma (preferably irradiated with 2500 rad) and 20% v/v of a commercially available medium.

Stem cells and resulting cells differentiated therefrom, directly obtained from the expansion method according to the invention, can be used as medicaments. Said medicaments can further include excipients and/or adjuvants and/or stabilizers and/or vehicles and can be formulated according to methods known in the art. The choice of such excipients and/or adjuvants and/or stabilizers and/or vehicles in the composition varies depending on the use, but it must maintain the suitability of the cells obtainable according to the method of the invention. The medicament can be in any dosage form known in the art and preferably the medicament is present in an injection liquid. The medicament can be administered by any way known in the art, preferably parenterally, such as an injection. In a preferred embodiment, said use as a medicament is for the preparation of a medicament for the transplantation of cells preferably belonging to the haematopoietic system and/or to the endothelial system, for regrowing again the population of cells belonging to the haematopoietic system and/or to the endothelial system at levels considered normal. Said application can be directed to people suffering from a lack of cells belonging to the haematopoietic system. Said lack can be due to the therapy of a pathology connected with the existing cells, such as for example due to a myelo- or lympho-ablative radiotherapy of a patient suffering from leukemia. Alternatively, if the cells belong to the endothelial system, said application can be directed to people suffering from vasculopathies caused by acute or chronic diseases (for example myocardium infarct or diabetic vasculopathy).

The advantages of using said cells in the preparation of such medicament is that cells are present in a significantly greater number, therefore people of any sizes can be treated and the rooting rate of cells to the bone marrow is improved.

In another preferred embodiment, said use as a medicament is for the preparation of a medicament for the treatment of malignant pathologies, such as for example acute or chronic leukemias or myelodisplastic syndromes, non malignant and congenital pathologies, such as for example serious combined immunodeficiencies, Wiskott-Aldrich syndrome, malignant osteoporosis, thalassaemia, Fanconi anemia, mucopolysaccharidoses and acquired non-malignant pathologies, such as for example serious aplastic anemia. Said medicaments can further contain excipients and/or adjuvants and/or stabilizers and/or vehicles and can be formulated according to methods known in the art. The choice of such excipients and/or adjuvants and/or stabilizers and/or vehicles in the composition varies depending on the use, but it must retain the suitability of the cells obtainable according to the method of the invention.

In another preferred embodiment, cells expanded according to the method of the invention can be used in a protocol of a gene therapy. By "gene therapy", in the context of the present invention, it is meant a method of an ex vivo gene therapy, including the following steps:
  withdrawing somatic cells from the concerned person
  culturing said cells
  transfecting the cells with the gene of interest during the culture, through a proper vector (for example a viral vector),
  optionally, isolating and growing in a culture only cells which have been transfected
  reintroducing the transfected cells in the body of the subject.

Said steps can be performed by using common techniques known in the art.

The gene therapy can be used for remedying to at least an aberrant gene trough the replacement or complementation with a wild-type gene, or for introducing an artificial gene for introducing a desired activity bound to a protein or the corresponding gene within the cell.

The use of a culture according to the invention for expanding the cells before or during or after the culture transfection, as above described, allows to improve the effectiveness of the whole therapy. In a still more preferred embodiment, the gene to be transfected is introduced within the cell before the expansion according to the method of the invention or with the culture according to the invention, in such a way that only useful and desired cells are expanded. Optionally, cells resulting from said transfection can then be used ex vivo, for the preparation of a medicament to be used in a specific protocol of a gene therapy. In another embodiment, the transfection introduces genes which render the stem cells (and consequently their descendants), when re-introduced in the human body, resistant to treatments which could be harmful for normal cells. An example known in the art consists of the "Multidrug resistance" (MDR) gene, which allows treatments with toxic or harmful materials for specific diseases in which it is not possible to define the treatment of the cells in a specific way.

In another embodiment of the invention, cells obtainable from the method according to the invention can be used for preparing autologous cell populations or autologous components ex vivo. For example, there can be used cells according to the invention for preparing platelet haemocomponents. Said preparation includes contacting the cells obtainable from the method according to the invention, for example through mixing, with a solution including thrombopoietin, interleukin-11, interleukin-6 and heparin. In this way, there is obtained the expansion of the cells $CD41^+$ and $CD61^+$, which are megacaryocyte immature parents which subsequently produce platelet haemocomponents.

Cells obtainable from the method according to the invention can be used in in vitro diagnostic assays for evaluating the effects of chemical compounds or environmental factors. The compounds include proteins or other kinds of molecules of a biological origin. Environmental factors include, for example, media utilizable for growing or maintaining cells in a suitable way, and fluids used in the preparations of said media. Said diagnostic assay could also be used for evaluating the harmfulness of new drugs before starting clinical protocols On a culture of just expanded cells.

Example 1

Experimental Protocol for the Expansion of Stem Cells $CD34^+$ i) At Day 0:
  A bag containing heat-inactivated allogenic plasma (HIAP) was placed under a hood and thawed at room temperature.
  An aliquot of umbilical cord blood was thawed and cells $CD34^+$ c were selected with the CliniMACS system, Milteny Biotech, Bergisch Gladbach, Germany. Said selection gave a population of cells $CD34^+$ of $0.36 \times 10^6$, equal to 88% of the total population of the selected cells.
  The volume of the culture medium (containing Medium CellGro, HIAP and cytokines) was calculated so as to have a cell concentration in the culture medium of $5 \times 10^3$ cells/mL.
  At the calculation result (72 mL) 10 ml were added, needed as a control tube.
  HIAP volume to be withdrawn was calculated in order to have a concentration of 10% (v/v) of the culture end volume.
  The volume of Medium CellGro to be withdrawn was calculated by subtracting the used HIAP volumes and each solution of cytokine. Cytokines must be at final concentrations of 10 ng/mL for IL6 and TPO, 50 ng/mL for SCF and FLT-3.
  The needed number of 10 mL tubes based on the quantity of medium calculated at the preceding point, was prepared and visually inspected for verifying the integrity.
  The following ingredients were withdrawn and transferred, under hood, in the following order: first, the quantity of Medium CellGro, then the quantity of HIAP and the quantity of cytokines computed in a single mixture. From said mixture 10 ml were withdrawn and introduced within the control tube (with reagents but without cells), which was therefore introduced within the incubator.
  1 ml of complete medium for each tube to be prepared was added to another tube containing the cells.
  9 mL of complete medium were dispensed within the tubes and successively 1 ml of cell suspension, collected from the cell-containing tube prepared in the preceding step, was added.
  Each tube was microscopically observed (with an inverted microscope) for finding possible anomalies and then the tubes were placed in the incubator at 37° C. and 5% $CO_2$.
ii) At Days 3; 7 and 10—Addition of Cytokines.
  At day 3, tubes were withdrawn from the incubator.
  A solution containing 100 ng of TPO, 100 ng of IL6, 500 ng of flt-3 and 500 ng of SCF for each 400 microL was prepared. 400 microL were added to each tube, including the control tube.
  Tubes were placed again within the incubator at 37° C. and 5% $CO_2$.
  At day 7, the operations were repeated.
  At day 10, the operations were repeated.
iii) At Day 14, Release of The Expanded Product
  In sterile conditions and under a hood, a physiological solution containing 2% p/v of human albumin e.v, was prepared, which constitutes the reinfusion buffer.
  All the tubes containing the expanding cells were collected from the incubator at the fourteenth day.
  A macroscopic (turgidity) and microscopic (with an inverted microscope) control of each tube was carried out.

After the control, the content of each tube was poured in 50 mL tubes, each tube was washed with total 5 mL of reinfusion buffer and the 5 mL added to the 50 mL tube containing the cell suspension.

A centrifugation at 1400 RPM for 10 minutes was carried out at room temperature.

At the end of the centrifugation the supernatant was separated in 50 mL tubes marked with the product code and the inscription "1° wash supernatant" and stored under a hood.

The pellet was re-suspended by adding 50 ml of reinfusion buffer and again centrifuged at 1400 RPM for 10 minutes at room temperature.

At the end of the centrifugation, the supernatant was separated in 50 mL tubes marked with the product code and the inscription "2° wash supernatant" and stored under a hood.

The resulting pellets were re-suspended and added to 50 ml of reinfusion buffer so as to form end tubes.

800 microL of cell suspension were withdrawn from said end tubes and a count of the total number of nucleated cells was performed in a Burker chamber. There were counted $124.6 \times 10^6$ nucleated cells on average.

Based on the mean concentration in the end tubes, 250,000 cells were withdrawn from the end tubes and analyzed through a cytofluorometry process.

The following tests were carried out on the 1° and 2° washes supernatant solutions:

sterility test, according to Eu. Ph. 2.6.1,

Culture test for microplasmas, according to Eu. Ph. 2.6.7, and

BACTEC test with Plus Aerobic/F* and Plus Anaerobic/F* Culture Vials Soybean-Case in Digest Broth, which are kits produced by Becton, Dickinson and Company-Come. Said kits allow fast methods for evaluating the microbial contamination of the cells, through the supernatant, before the release, according to GMP.

LAL chromogenic test, according to Eu. Ph. 2.6.14. At the day zero, $0.36 \times 10^6$ cells CD34+ (with a 880 purity) were selected for expansion.

After the expansion, through a fluorocytometry method, a total population of nucleated cells of $124.6 \times 10^6$ was counted, in which there were present $9.97 \times 10^6$ cells CD34+, $9.06 \times 10^6$ cells CD3133+; $0.007 \times 10^6$ cells CD19+; $0.007 \times 10^6$ cells NK; $0.017 \times 10^6$ cells CD3+ and $1.4 \times 10^6$ cells CD61+.

Example 2

Transplantation of Cells Expanded According to the Invention in a Child Suffering from Thalassaemia, One Suffering from Sickle Cell Anemia and in a Child Suffering from Refractory Anemia Three children suffering from thalassaemia (PT1); sickle cell anemia (PT2) and refractory anemia (PT3) were transfused with blood collected from thawed umbilical cord after an expansion carried out as described in the Example 1.

Table 2 shows the expansion results of said cells. Before the expansion, the selection for the cells CD34+ was performed as above described.

TABLE 2

Results of expansions on three aliquots of thawed umbilical cord blood for transfusion in three patients:

| | | PT1 | PT2 | PT3 |
|---|---|---|---|---|
| | Age (years)/Sex | 5/Male | 9/Female | 7/Male |
| | Body weight (BW) of the patient (Kg) | 15 | 29 | 25 |
| Units of non expanded umbilical cord blood | Number of nucleated cells/BW (Kg) | $24 \times 10^6$ | $16 \times 10^6$ | $23 \times 10^6$ |
| | Number of cells CD34+/BW (Kg) | $2.4 \times 10^5$ | $1.2 \times 10^5$ | $1.2 \times 10^5$ |
| | Number of cells CD3+/BW (Kg) | $8.9 \times 10^6$ | $6.1 \times 10^6$ | $7.4 \times 10^6$ |
| Units of expanded umbilical cord blood | Number of nucleated cells/BW (Kg) | $8.0 \times 10^6$ | $4.3 \times 10^6$ | $2.3 \times 10^6$ |
| | Number of cells CD34+/BW (Kg) | $6.7 \times 10^5$ | $4.7 \times 10^5$ | $2.3 \times 10^5$ |
| | Number of cells CD133+/BW (Kg) | $1.4 \times 10^5$ | $3.5 \times 10^5$ | $2.1 \times 10^5$ |
| | Number of cells CD3+/BW (Kg) | $1.0 \times 10^3$ | $1.0 \times 10^3$ | Non detectable |
| Units of expanded umbilical cord blood | Number of cells CD19+/BW (Kg) | Non detectable | Non detectable | Non detectable |
| | Number of cells CD56+/BW (Kg) | Non detectable | $2.0 \times 10^3$ | $1.0 \times 10^3$ |
| | Number of cells CD61+/BW (Kg) | $1.0 \times 10^5$ | $4.6 \times 10^4$ | $5.4 \times 10^4$ |

In all the three patients, the hystocompatibility was determined through low resolution serology or typification for antigens HLA-A or -B and high resolution typification of the DNA for HLA-DRB1. Anti-thymocyte globulin (ATG) was transplanted daily from donors not connected to a dosage of 3 mg/kg daily from four days until two days before the transplantation.

GVHD, graft-versus-host-disease, was classed according to methods known in the art (Glucksberg H et al., Clinical manifestations of graft-versus-host disease in human recipients of bone marrow from HLA-matched sibling donors, Transplantation, 1974; 18; 295-304 and 19 and Storb R et al. Predictive factors in chronic graft-versus-host disease in patients with aplastic anemia treated by bone marrow transplantation from HLA-identical siblings, Ann Intern Med 1983; 98: 461-466). For the conditioning therapy and the prophylaxis of GVHD the same drugs currently in use for a trans-plantation of non manipulated placental blood from a familial donor or from a non consanguineous donor were used. The conditioning methods have foreseen the administration of the following drugs in different combinations and according to different administration plans, generally starting about 3 weeks before the transplantation: Busulfane, Thiotepa, Fludarabine, Cyclophosphamide, Melfalan. Shortly, the GVHD prophylaxis is articulated on the use of Cyclosporin-A, steroids and anti-lymphocyte serum.

It has been established that the rooting of myeloids was successfully carried out when neutrophils were observed at a concentration above $0.5 \times 10^9$/L for three consecutive days and the rooting of platelets when a concentration of more than $30 \times 10^9$/L for nine consecutive days was observed.

All the three patients are alive and without any pathological complications after 29 months, 22 months and 19 months after the transplantation for PT1, PT2 and PT3, respectively. The results concerning the relative clinical outcomes are reported in Table 3. Expanded cells, in form of a sterile and apyrogenic cell suspension in a saline solution for e.v. use and human albumina, were withdrawn with a syringe, in sterility and under hood and the cells were generally administered through the central venous way used for the therapy.

TABLE 3

Clinical outcome of transplantation with cells of umbilical cord blood expanded according to the invention in children with haematopoietic diseases.

| | PT1 | PT2 | PT3 |
|---|---|---|---|
| Outcome after 15 months | Alive and in a relative good clinical condition | Alive and in a relative good clinical condition | Alive and in a relative good clinical condition |
| Day in which the rooting of myeloids (>0.5 × $10^9$/L) was observed | 16 | 18 | 29 |
| Day in which the rooting of platelets (>30 × $10^9$/L) was observed | 31 | 33 | 59 |
| Acute GVHD | No | No | Yes |
| Chronic GCHD | No | No | No |
| Serious viral, bacterial or mycotic infections | No | No | No |
| Re-development of the pathologies | No | No | No |

It has to be noted that said very good results should not have been possible if one considers that, for all the three children the umbilical cord blood were not enough, if it were not expanded according to the method of the invention with the culture according to the invention. In all the three cases, the level of cells in the umbilical cord blood was lower than $3.7 \times 10^7$ cells nucleated for each kg of the patient, and as shown by Gluckman et al. (Gluckman E et al. for Eurocord Transplant Group and European Blood and Marrow Transplant Group (EBMT). Clinical outcome in recipients of cord blood transplant from related and unrelated donors. N Engl J Med 1997; 337:373-381) for having a positive outcome in the transplantation from umbilical cord blood, at least $3.7 \times 10^7$ nucleated cells for each kg of patient are needed.

Said example shows the positive outcome in a short-medium term, but it apply equally at the long term as known in the art and shown by Locatelli F et al. (Locatelli F et al. Related umbilical cord blood trans-plant in patients with Thalassemia and Sickle Cell Disease, Blood, 2003; 101:2137-43).

Example 3

Control for Chromosomal Anomalies in Cells After the Expansion

On chromosomal preparations of the cultured cells at 14 days of expansion, as reported in the Example 1, chromosomes were fluorescence analyzed with a QF band and with differential colorations for the purpose of identifying structural anomalies both numerical (such as trisomies, monosomies) and structural (translocations, deletions and inversions).

In the expanded cells, chromosomic anomalies were not observed.

Example 4

Expansion on Pluripotent Stem Cells

"Embryoid Bodies" (EB) cells were prepared by growing parthenogenic cells with a "hanging droplets" method in a culture containing a glucose-low concentration medium DMEM/F10 (1:1) with 2 mM glutamine added, 0.1 mM 2-mercaptoethanol, 75 µg/ml penicillin and 50 µg/ml streptomycin, 1% p/v non essential amino acids (Gibco, Invitrogen, Italy), 1% p/v nucleosides mix, 10% v/v Knock-out serum replacer (Gibco Invitrogen Italy) and 5% v/v FBS (Gibco, Invitrogen Italy) for 9 days, in which each day the medium was returned at the starting concentrations of ingredients.

EBs were dissociated in a sterile environment and prepared in an expansion medium according to a method similar to the Example 1, wherein the only difference was the length of three weeks instead of two. Therefore, the medium was restored with the cytokines mixture at $14^{th}$ and $17^{th}$ days and the expanded product was released at the $21^{st}$ day. From an initial population of 8400 EB cells, 219000 EB cells were counted after 3 weeks with a cytofluorometric method.

The invention claimed is:

1. A serum-free culture medium comprising a composition of cytokines consisting of:
   i) interleukin-6 (IL6);
   ii) flt3-ligand (FLT3);
   iii) stem cell factor (SCF);
   iv) thrombopoietin (TPO);
   in the absence of any other cytokine.

2. The culture medium according to claim 1, wherein the cytokine IL6 is at a concentration between 1 and 20 ng/ml.

3. The culture medium according to claim 1, wherein the cytokine IL6 is at a concentration between 5 and 15 ng/ml.

4. The culture medium according to claim 1, wherein the cytokine IL6 is at a concentration between 9 and 11 ng/ml.

5. The culture medium according to the claim 1, wherein the cytokine FLT3 is at a concentration between 20 and 80 ng/ml.

6. The culture medium according to claim 1, wherein the cytokine FLT3 is at a concentration between 35 and 65 ng/ml.

7. The culture medium according to claim 1, wherein the cytokine FLT3 is at a concentration between 49 and 51 ng/ml.

8. The culture medium according to claim 1, wherein the cytokine SCF is at a concentration between 20 and 80 ng/ml.

9. The culture medium according to claim 1, wherein the cytokine SCF is at a concentration between 35 and 65 ng/ml.

10. The culture medium according to claim 1, wherein the cytokine SCF is at a concentration between 49 and 51 ng/ml.

11. The culture medium according to claim 1, wherein the cytokine TPO is at a concentration between 1 and 20 ng/ml.

12. The culture medium according to claim 1, wherein the cytokine TPO is at a concentration between 5 and 15 ng/ml.

13. The culture medium according to claim 1, wherein the cytokine TPO is at a concentration between 9 and 11 ng/ml.

* * * * *